US010244758B2

(12) United States Patent
Worthington et al.

(10) Patent No.: US 10,244,758 B2
(45) Date of Patent: Apr. 2, 2019

(54) COMPOSITIONS COMPRISING A GERMINANT AND AN ANTIMICROBIAL AGENT

(71) Applicant: Insight Health Limited, Middlesex (GB)

(72) Inventors: Tony Worthington, West Midlands (GB); Laura Wheeldon, West Midlands (GB)

(73) Assignee: Insight Health Limited (GB)

( * ) Notice: Subject to any disclaimer, the term of this patent is extended or adjusted under 35 U.S.C. 154(b) by 0 days.

(21) Appl. No.: 15/046,045

(22) Filed: Feb. 17, 2016

(65) Prior Publication Data
US 2016/0157490 A1 Jun. 9, 2016

Related U.S. Application Data

(63) Continuation of application No. 13/579,121, filed as application No. PCT/GB2011/050278 on Feb. 15, 2011, now Pat. No. 9,314,028.

(30) Foreign Application Priority Data

Feb. 16, 2010 (GB) .................................. 1002594.8
Mar. 8, 2010 (GB) .................................. 1003799.2

(51) Int. Cl.
| A01N 45/00 | (2006.01) |
| A01N 47/44 | (2006.01) |
| A01N 31/04 | (2006.01) |
| A01N 33/12 | (2006.01) |
| A01N 37/44 | (2006.01) |
| A01N 43/50 | (2006.01) |
| A01N 25/08 | (2006.01) |
| A01N 37/50 | (2006.01) |

(52) U.S. Cl.
CPC ............ A01N 45/00 (2013.01); A01N 25/08 (2013.01); A01N 31/04 (2013.01); A01N 33/12 (2013.01); A01N 37/44 (2013.01); A01N 37/50 (2013.01); A01N 43/50 (2013.01); A01N 47/44 (2013.01)

(58) Field of Classification Search
CPC ................................ A01N 33/12; A01N 47/44
See application file for complete search history.

(56) References Cited

U.S. PATENT DOCUMENTS

| 6,656,919 | B1 | 12/2003 | Baugh et al. | |
| 6,875,288 | B2 | 4/2005 | Gotoh et al. | |
| 2001/0051595 | A1 | 12/2001 | Lyons et al. | |
| 2003/0072807 | A1 | 4/2003 | Wong et al. | |
| 2004/0185123 | A1* | 9/2004 | Mazzio .................. | A61K 36/28 424/730 |
| 2005/0048126 | A1 | 3/2005 | Rabinow et al. | |
| 2006/0083768 | A1* | 4/2006 | Labrecque ................ | A61F 2/90 424/423 |
| 2008/0118544 | A1* | 5/2008 | Wang .................... | A61K 31/337 424/423 |
| 2008/0254010 | A1 | 10/2008 | Sasser et al. | |
| 2011/0135702 | A1 | 6/2011 | Hoffman et al. | |

FOREIGN PATENT DOCUMENTS

| WO | 03061610 A1 | 7/2003 |
| WO | 2008156636 A1 | 12/2008 |

OTHER PUBLICATIONS

Wheeldon et al., "Antimicrobial efficacy of copper surfaces against spores and vegetative cells of Clostridium difficile: the germination theory", Journal of Antimicrobial Chemotherapy, vol. 62, Jun. 10, 2008 (Jun. 10, 2008), pp. 522-525, XP002636057, DOI: 10.1093/jac/dkn219.
Wheeldon et al., "P9.01 Susceptibility of Germinating Clostridium difficile Spores to 70% Ethanol", Journal of Hospital Infection, Academic Press, London, GB, vol. 64, Jan. 1, 2006 (Jan. 1, 2006). p. S47, XP005843824, ISSN: 0195-6701, DOI: 10.1016/S0195-6701(06)60152-7.
Lowden et al., "Germinate to exterminate: Susceptibility of germinating spores of Clostridium difficile ribotype 027 to desiccation and aerobic conditions", 19th European Congress of Clinical Microbiology and Infectious Diseases, Helsinki, Finland, May 16-19, 2009, P1260, May 16, 2009 (May 16, 2009), XP002636053, Blackwell Publishing, Retrieved from the Internet: U RL:http://www.blackwellpiublishing.com/eccmid19/abstract.asp?id=74866 [retrieved on May 9, 2011].
Sorg et al., "Bile Salts and Glycine as Cogerminants for Clostridium difficile Spores", Journal of Bacteriology, vol. 190, No. 7, Feb. 1, 2008 (Feb. 1, 2008), pp. 2505-2512, XP002636062, ISSN: 0021-9193, DOI: 1 0.1128/JB.01765-07.
Wheeldon et al., "Physical and chemical factors influencing the germination of Clostridium difficile spores", Journal of Applied Microbiology, vol. 105, No. 6, Nov. 19, 2008 (Nov. 19, 2008), p. 2223, XP002636137, DOI: 10.1111/0365-2672.2008.03965.x.
U.S. Food and Drug Administration: "M146 Thioglycollate Medium Fluid (FTG)", Bacteriological Analytical Manual, 8th Edition, revision A, 1998, Jan. 1, 2001 (Jan. 1, 2001), XP002636427, Retrieved from the Internet: URL:http://www.fda.gov/Food/ScienceResearch/LaboratoryMethods/BacteriologicalAnalyticalManualBAM/UCM063688 [retrieved on May 16, 2011].
Condalab Pronadisa Micro & Molecular Biology: "Yeast Extract Cat No. 1702—Ingredients Extract", Laboratorios Conda, S.A., Apr. 30, 2006 (Apr. 30, 2006), XP002636426, Retrieved from the Internet: URL:http://replay.web.archive.org/20060430175826/http://www.condalab.com/index_eng.htm [retrieved on May 12, 2011].

(Continued)

Primary Examiner — Kyle A Purdy
(74) Attorney, Agent, or Firm — Lerner, David, Littenberg, Krumholz & Mentlik, LLP

(57) ABSTRACT

The present invention provides an antiseptic composition comprising a germinant and an antimicrobial agent, wherein the germinant increases a pathogen's susceptibility to attack from the antimicrobial agent and wherein the antimicrobial agent does not inhibit the germinant. The present invention also provides an antiseptic wipe, handwash or paint comprising such antiseptic composition and a method of sterilizing a surface using such a composition.

10 Claims, 11 Drawing Sheets

(56) References Cited

OTHER PUBLICATIONS

Figure 1:
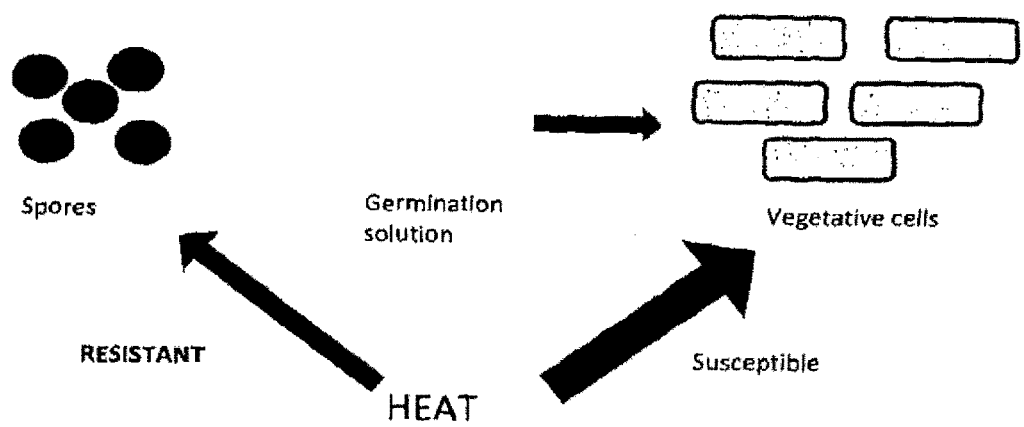
Figure 2:
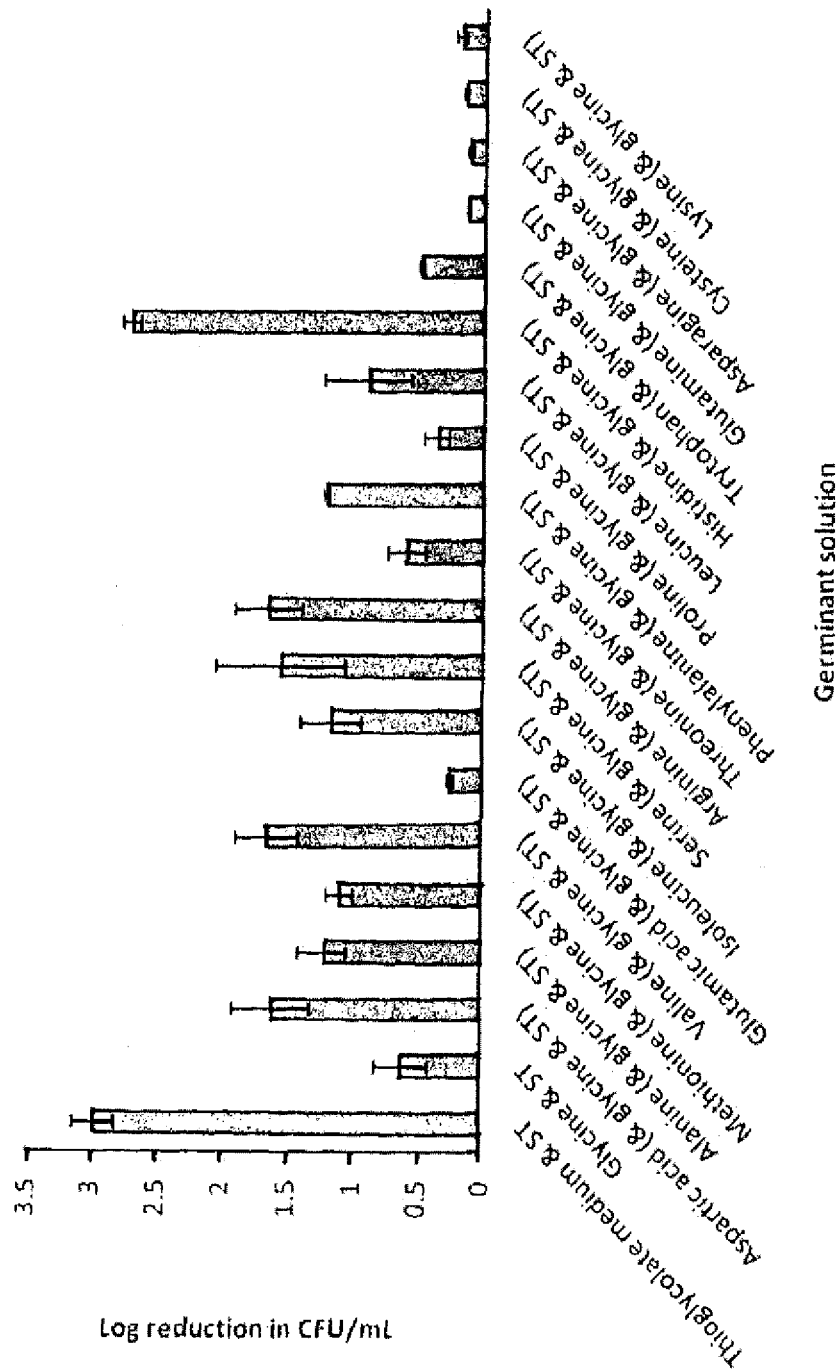
Figure 3:
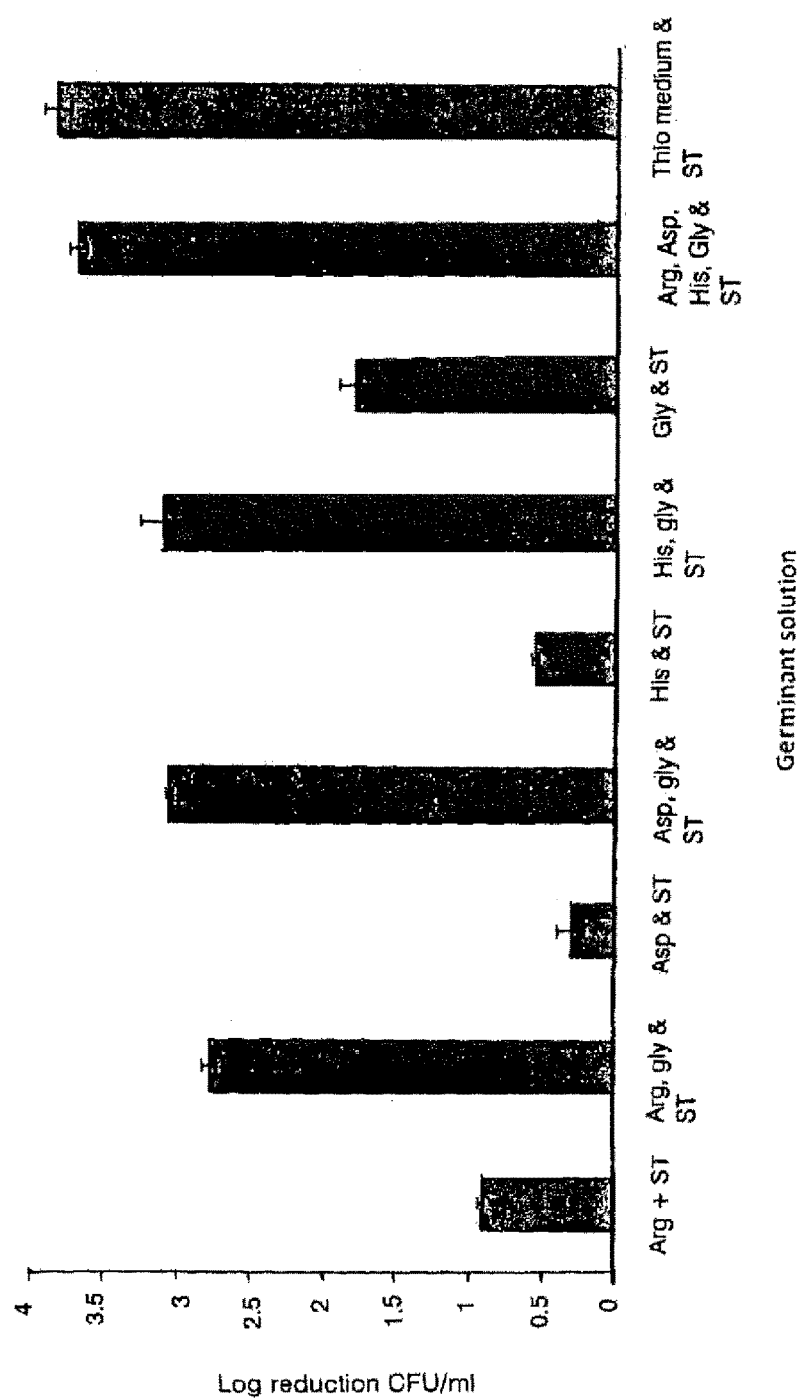
Figure 4:
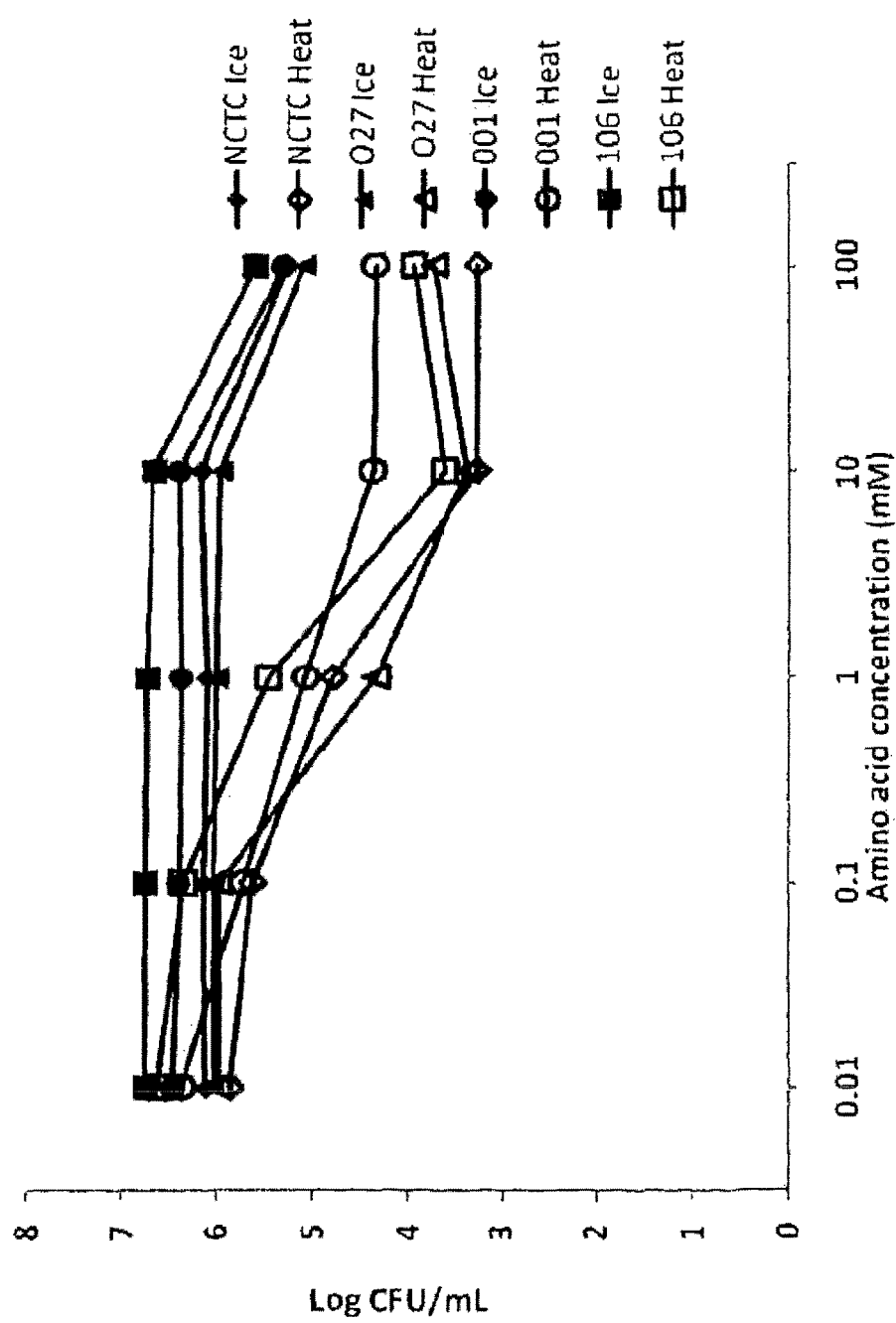
Figure 5:
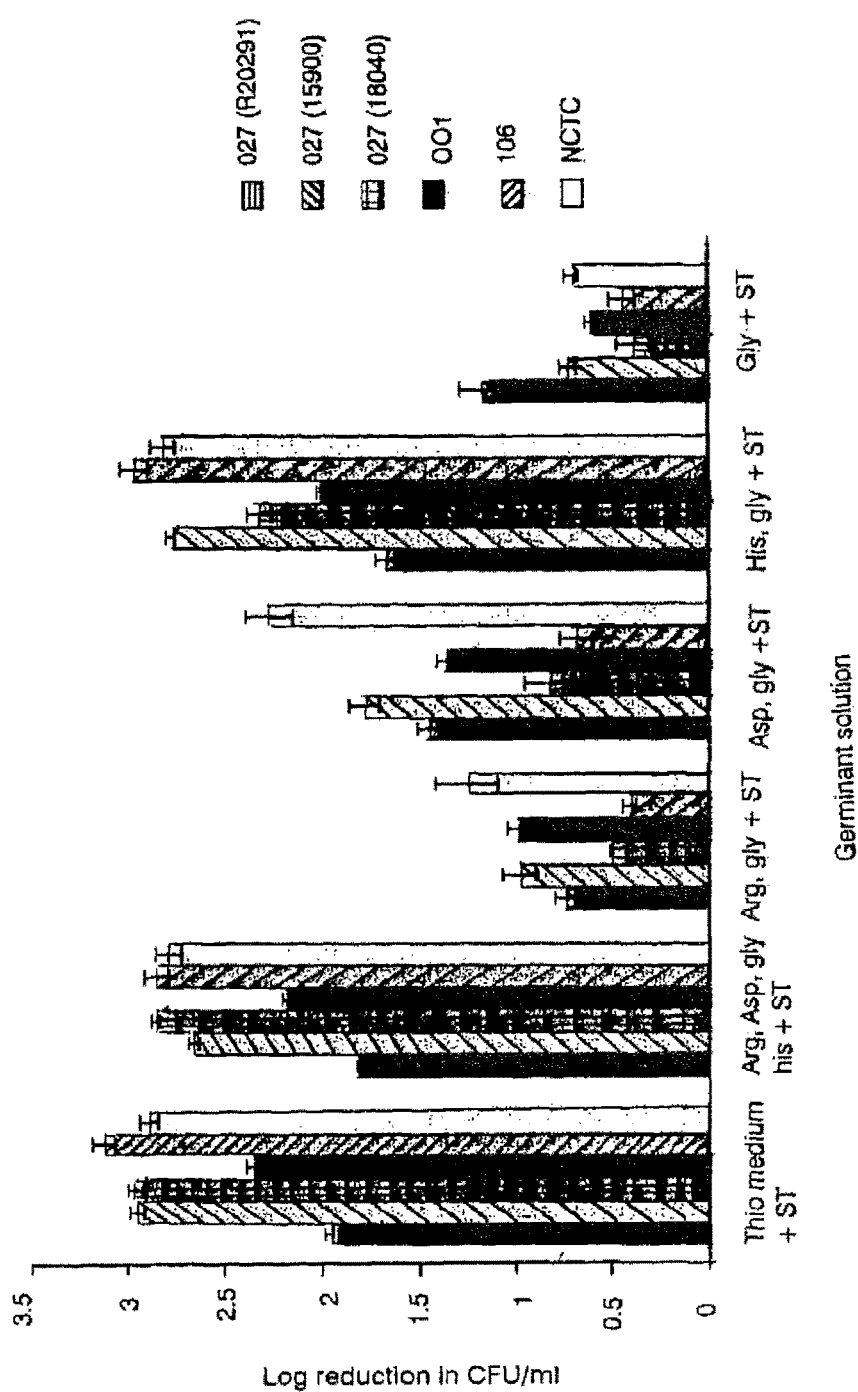
Figure 6:
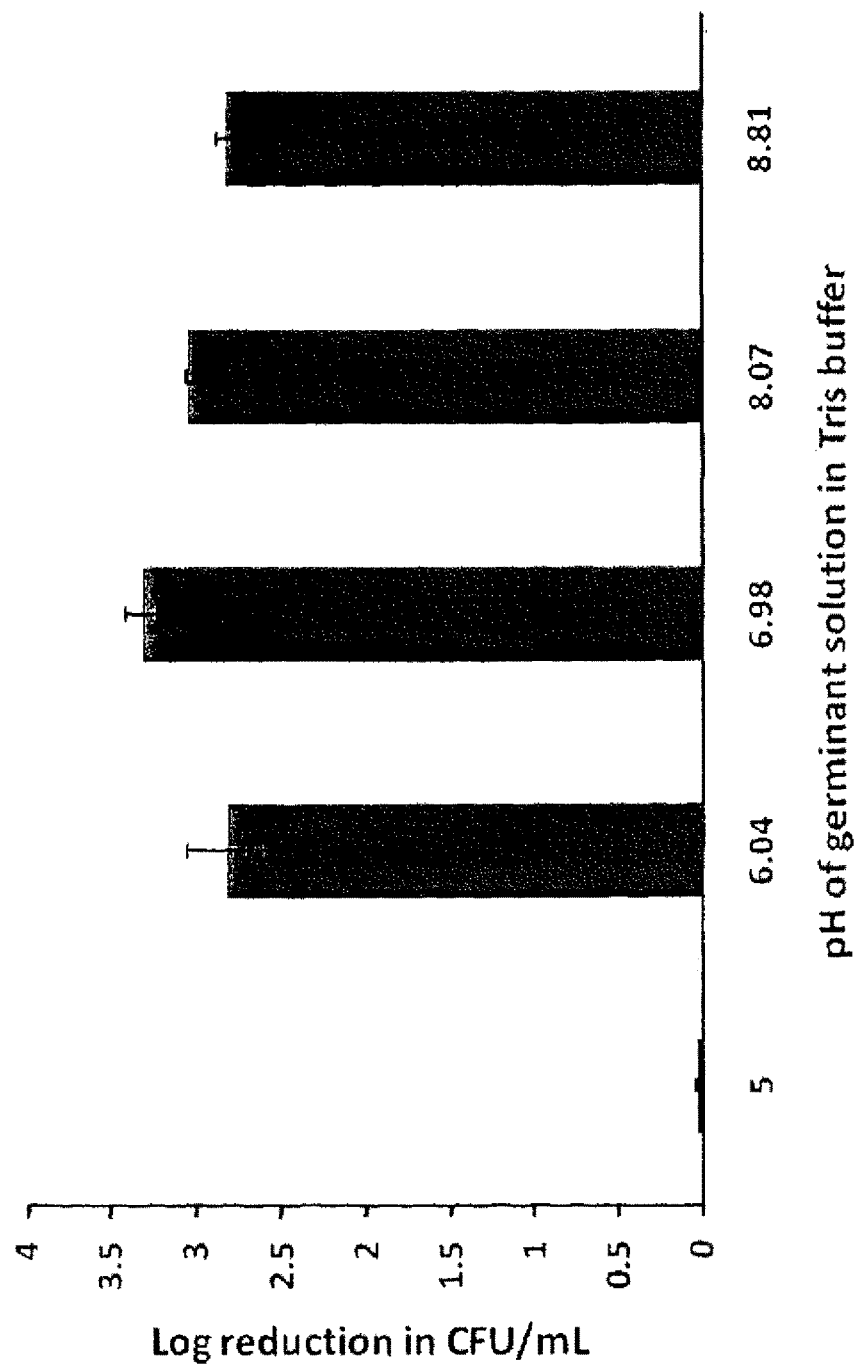
Figure 7:
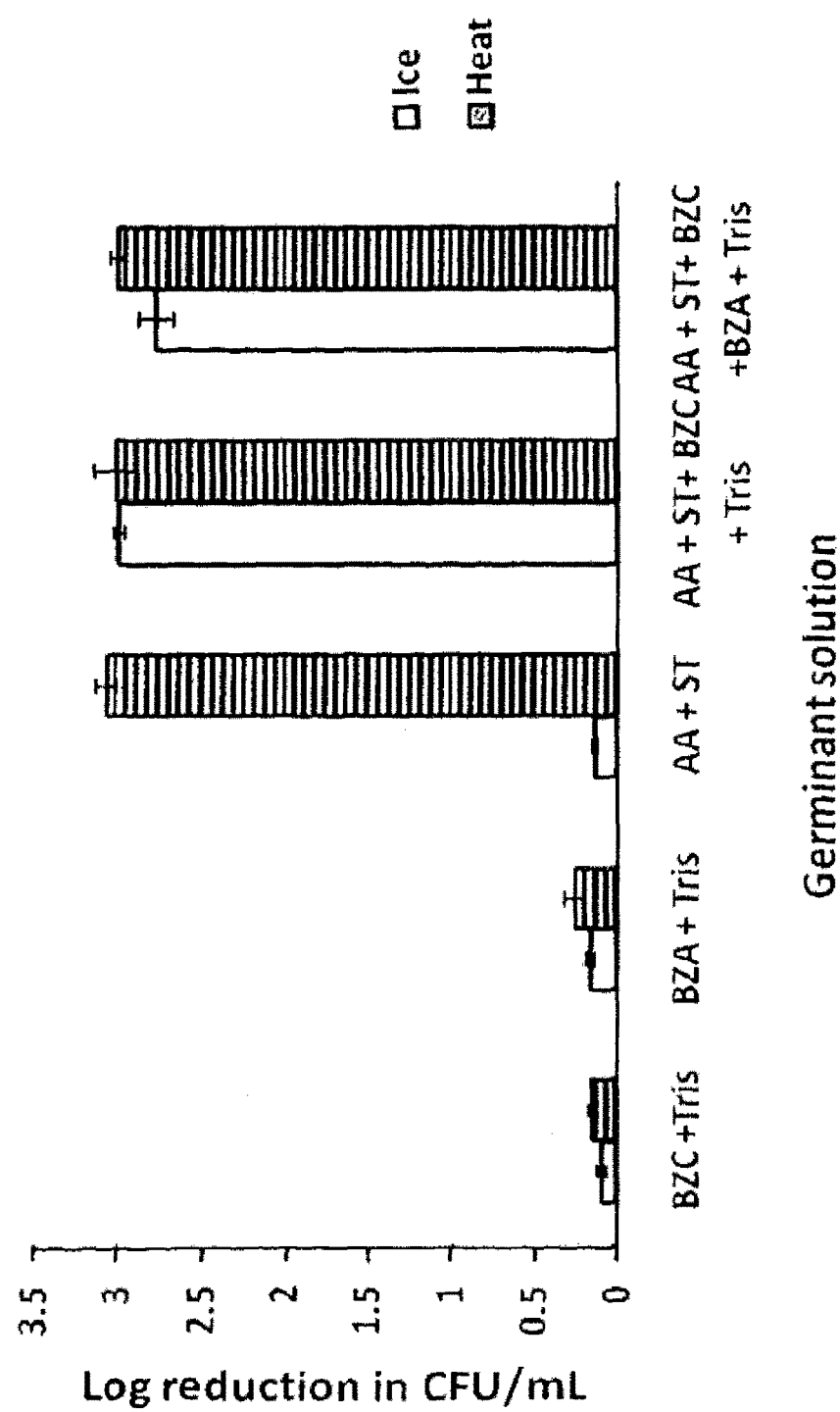
Figure 8:
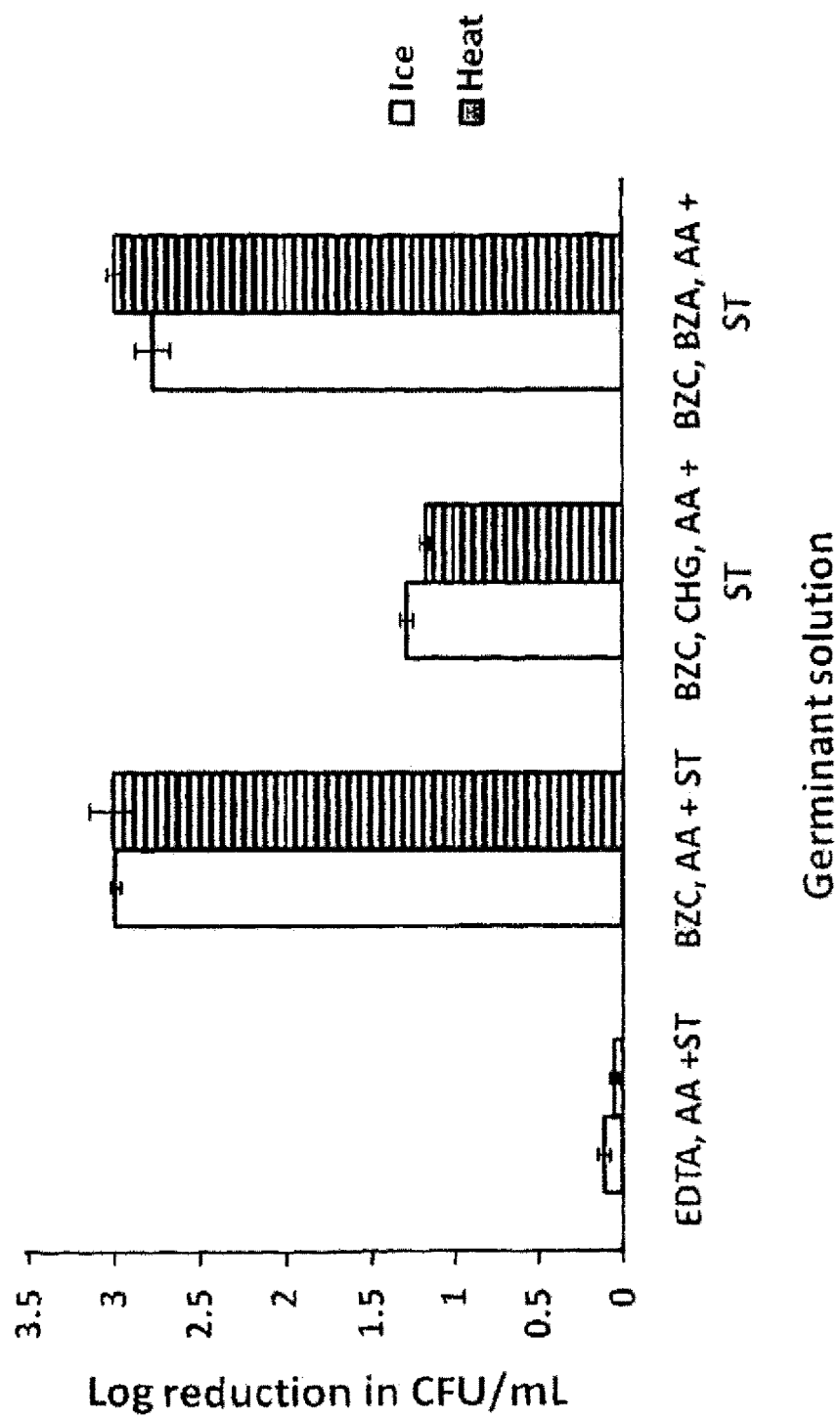
Figure 9:
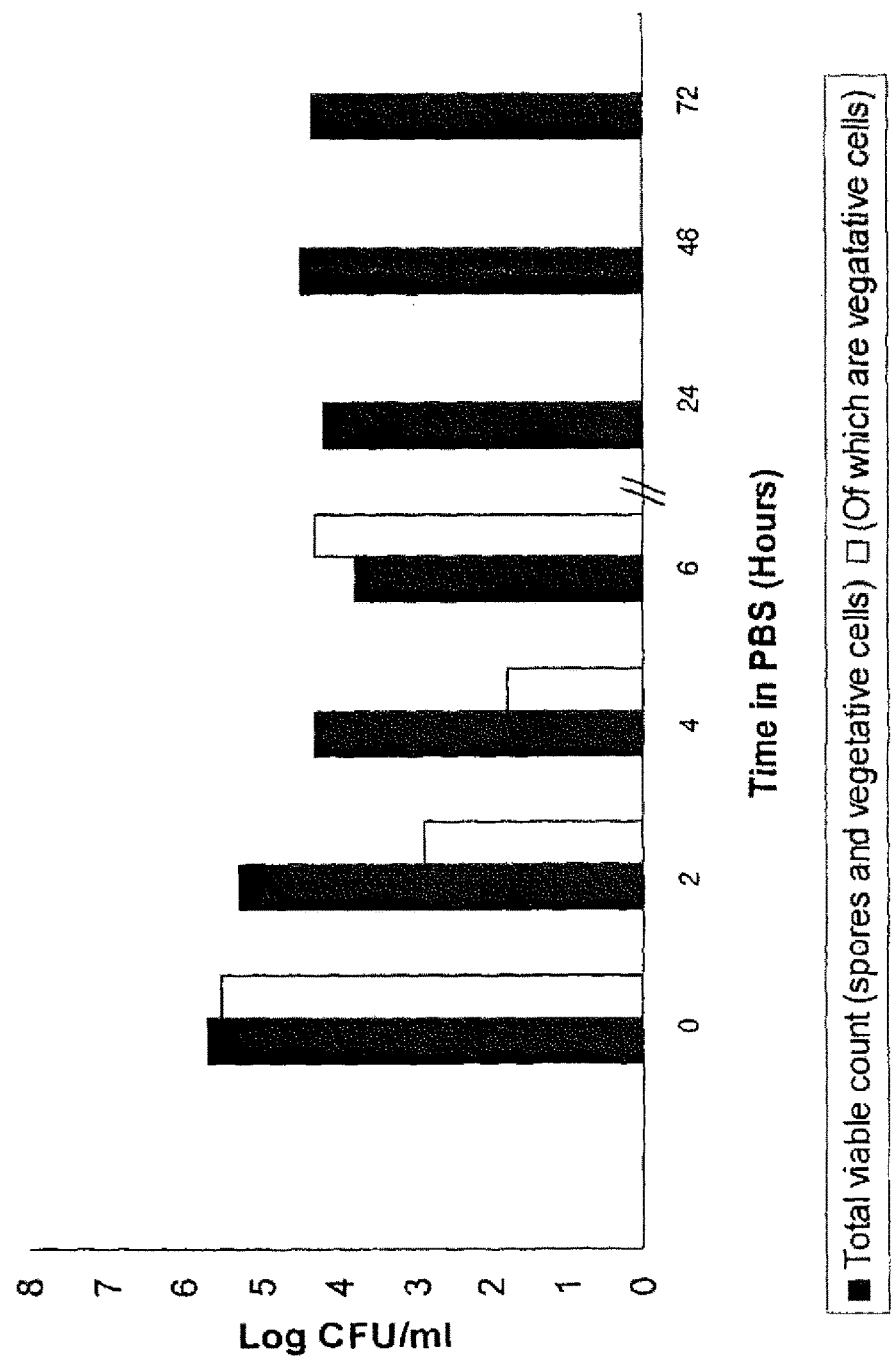
Figure 10:
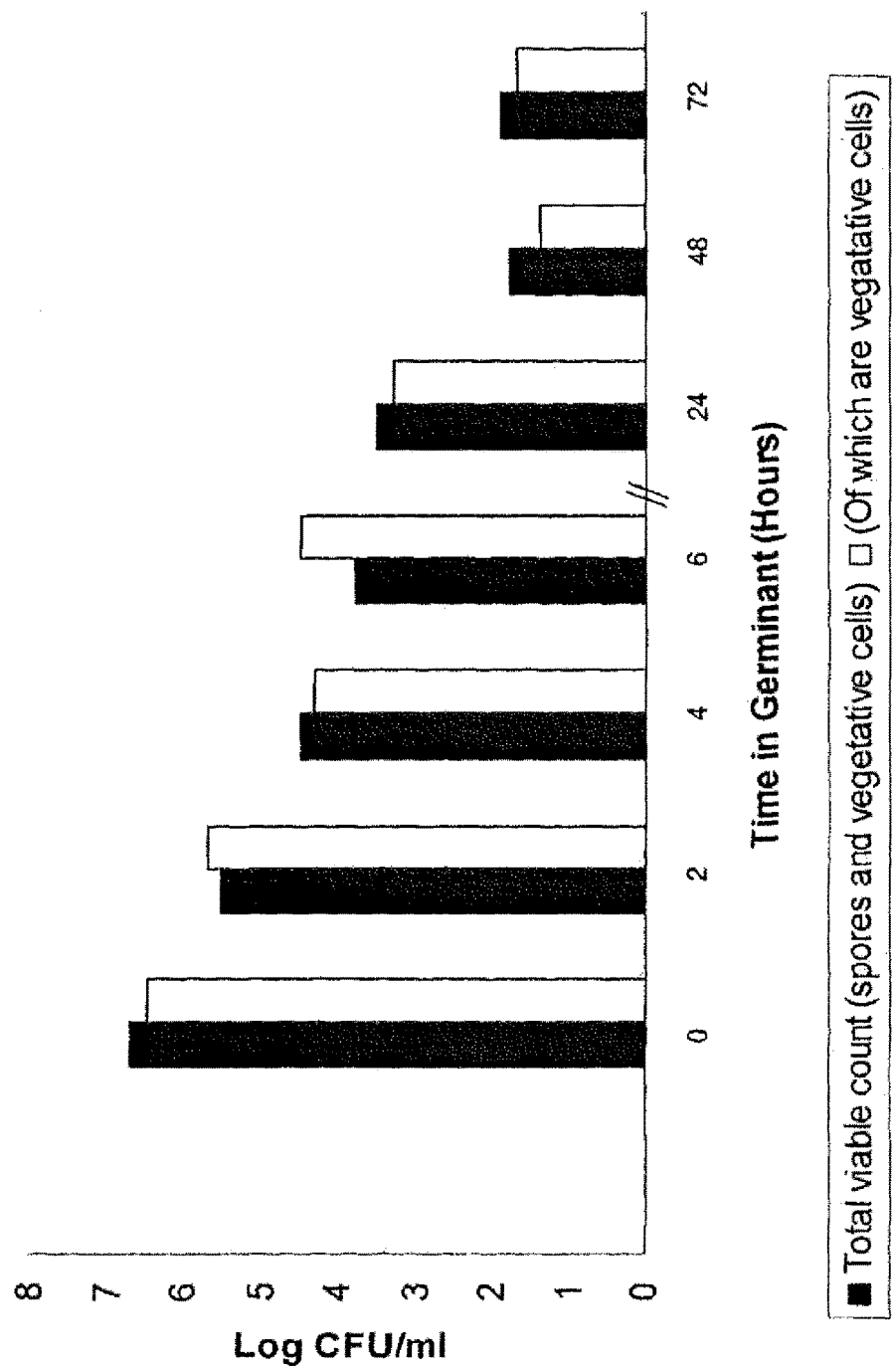

International Search Report and Written Opinion for Application No. PCT/GB2011/050278 dated Jul. 6, 2011.
Wheeldon L et al: "P13.06 Germinate to exterminate: a novel way of eliminating Clostridium difficile spores", Journal of Hospital Infection, vol. 76, Oct. 1, 2010 (Oct. 1, 2010), p. S43, XP027367150, Academic Press, London, GB ISSN: 0195-6701 [retrieved on Oct. 1, 2010].
Wheeldon et al., "Histidine acts as a co-germinant with glycine and taurocholate for Clostridium difficile spores.", Journal of Applied Microbiology, vol. 110, Feb. 18, 2011 (Feb. 18, 2011), pp. 987-994, XP002636080, DOI: 10.1111/j.1365-2672.2011.04953.x the whole document.

* cited by examiner

Table 1

| Germinant solution | Log reduction in CFU/mL after 1hr incubation followed by chilling on ice | Log reduction in CFU/mL after 1hr incubation followed by heat shocking |
|---|---|---|
| Benzalkonium chloride and Tris | 0.09 | 0.14 |
| Benzyl alcohol and Tris | 0.16 | 0.25 |
| Amino acids, taurocholate and Tris | 0.13 | 3.07 |
| Amino acids, taurocholate, benzalkonium chloride, benzyl alcohol and Tris | 2.77 | 2.99 |

FIG. 11

COMPOSITIONS COMPRISING A GERMINANT AND AN ANTIMICROBIAL AGENT

CROSS-REFERENCE TO RELATED APPLICATIONS

The present application is a continuation of U.S. patent application Ser. No. 13/579,121, filed on Aug. 15, 2012, which is a national phase entry under 35 U.S.C. § 371 of International Application No. PCT/GB2011/050278, filed Feb. 15, 2011, published in English, which claims the benefit of GB Application No. 1003799.2, filed Mar. 8, 2010 and GB Application No. 1002594.8, filed Feb. 16, 2010. The disclosures of all of said applications are incorporated by reference herein.

FIELD OF THE INVENTION

The present invention relates to compositions having antimicrobial properties and methods of disinfecting surfaces using such compositions. More specifically, the present invention relates to compositions which have effective antimicrobial activity against spore forming pathogens.

BACKGROUND OF THE INVENTION

Spore forming pathogens, such as *C. difficile*, are important infectious agents. *C. difficile* is the leading cause of nosocomial diarrhoea in the UK and has been responsible for a significant number of deaths in UK hospitals. Recent figures show a decline in the number of cases in *C. difficile* infection. However, despite this decrease there are still nearly 10 times as many cases of *C. difficile* compared to MRSA. PCR ribotype 027 is now the most common ribotype isolated from *C. difficile* patients, followed by ribotype 106 and 001.

Infected patients excrete large numbers of *C. difficile* spores and cells into the environment which acts as a reservoir of infection. Patients therefore generally acquire the organism by ingestion of its spores from the contaminated environment. Once ingested the spores are able to survive the acidic environment of the stomach and pass into the GI tract where they germinate into vegetative cells to produce toxins A and B, which may cause disease in susceptible patients.

Spore germination is an irreversible process in which a highly resistant, dormant spore is transformed into a metabolically active cell. Germination occurs in several stages; the first being activated by the binding of germinant receptor on the plasma membrane. This is then followed by the loss of heat resistance and various cations including potassium, hydrogen and sodium and the complex of calcium and dipicolinic acid (DPA). This results in the partial re-hydration of the core, however the organism does not become fully hydrated until the cortex is degraded. As the cortex hydrolyses, the small acid soluble proteins are degraded and the metabolic activity of cell is resumed.

It is known in the art that *C. difficile* may be simulated to sporulate by exposure to germination solutions comprising a combination of glycine and taurocholate. The transition from the spore state causes the pathogens to be susceptible to attack from antibacterial agents, such chlorhexidine. The aim of the prior art has been to design germinate/exterminate protocols which take advantage of the susceptibility of the pathogen following germination. Such a protocol is shown in FIG. 1. Specifically, attempts have been made in the prior art to design antibacterial solutions which stimulate germination and which have an antibacterial agent to attack the germinated pathogens. However, the antibacterial agents used in such approaches have an inhibitory effect on the germinating solution such that germinate/exterminate approach has had limited success in the clinical setting.

The aim of the present invention is there to provide an alternative antimicrobial composition which overcomes these problems and which is effective against clinically important pathogens.

SUMMARY OF THE INVENTION

The inventors of the present invention have found that particular compositions comprising combinations of amino acids with sodium taurocholate have enhanced sporulating activity compared to the prior art compositions of glycine only in combination with taurocholate. Furthermore, the inventors have discovered that particular antimicrobial agents are able to kill the germinated spores effectively whilst acting as a preservative in the composition. These agents do not have an inhibitory effect on the germination of the pathogen observed in the prior art antimicrobials used in the germinate/exterminate approach.

Furthermore, the inventors of the present invention have found that, as well as stimulating the formation of vegetative cells from spores of *C. difficile*, the compositions of the present invention prevent sporulation of vegetative cells of *C. difficile*. This is particularly advantageous in the clinical environment. Many vegetative cells (as well as spores) are excreted in the faeces of hospitalised patients. The vegetative cells will eventually sporulate and the spores then act as a vector of transmission of disease. Keeping the cells in the vegetative form is preferred since they will be naturally killed by air, as they are strictly anaerobic, or common hard surface disinfectants used in hospitals. The compositions of the present invention therefore have a two way attack; first, converting pores into vegetative cells and, second, holding vegetative cells in the vegetative form.

In a first aspect, the present invention provides an antiseptic composition comprising a germinant and an antimicrobial agent, wherein said germinant increases a pathogen's susceptibility to attack from the antimicrobial agent and wherein the antimicrobial agent does not inhibit the germinant.

In a second aspect, the present invention provides an antiseptic wipe comprising a fabric, mesh or gauze type material impregnated with a composition of the invention. In a third aspect, the present invention provides an antiseptic hand wash or paint for coating on an abiotic surface which handwash or paint comprises a composition of the invention.

In a fourth aspect, the present invention provides a method of disinfecting a surface such that it is essentially free of pathogens, the method comprising contacting the surface with the composition of the invention or an antimicrobial wipe or paint comprising a composition of the invention for a time sufficient for the pathogens to germinate and be killed.

The antiseptic composition of the present invention comprises a germinant in combination with an antimicrobial agent. The germinant is selected from at least two amino acids. Preferably the amino acids are the combination of histidine, arginine, aspartic acid, glycine. More preferably the combination of amino acids is histidine, arginine, aspartic acid, glycine and valine. This particular combination of amino acids has been shown by the inventors to be particularly advantageous having increased germination effects on bacterial spores.

The germinant is provided in an amount suitable to stimulate effective sporulation of the spores. Preferably, the germinant is provided in an amount of from 1 to 10 mM based on the final composition. The constituent amino acids within the germinant solution may be provided in an amount of 50 mM (histidine), 50 mM (glycine), 50 mM (arginine), 50 mM 1:50 (valine) and 50 mM (aspartic acid).

The antimicrobial agent is an agent which is effective at killing a pathogenic microorganism upon its contact with a surface on which the pathogen is found. Preferably, the antimicrobial agent is effective or killing the pathogen when it is in the germination state following sporulation. The antimicrobial agent may also be effective at killing pathogens which do no form spores.

Preferably, the antimicrobial agent is a combination of benzalkonium chloride and benzyl alcohol. The ratio of benzalkonium chloride to benzyl alcohol in the antiseptic composition is 1:50. The antimicrobial agent is provided (with respect to the total amount of antimicrobial agent in the antiseptic composition) in an amount of from 0.01% to 2%.

The antiseptic composition may be provided in a form required for use to disinfect surfaces in the clinical environment. Preferably such surfaces are abiotic surfaces. Alternatively, the surface may be the skin of a patient, doctor or carer. Preferably, the composition is provided in the form of a liquid, gel, foam or spray which may be conveniently applied to a surface requiring treatment. In a further embodiment, an antimicrobial wipe is provided comprising a fabric, mesh or gauze type material impregnated with the antiseptic composition. The composition may also be provided in tablet form. Such tablet forms may be dissolved in a suitable amount of water and the resultant solution used as a disinfecting agent by hospital cleaners, for example, in cleaning large surface areas. In the embodiment where the surface is a person's skin, then the antiseptic composition may be in the form of a handwash or wipe. Preferably, the antiseptic composition is in the form of a paint which may be painted on to the surface to be treated. Such a paint is particularly advantageous since once dried it is effective at killing pathogens over a longer period of time compared to prior art antiseptics which are ineffective once dried and which the antimicrobial agent leads to inhibition of the germinating agent after a particular length of time. Even more preferably the antiseptic is in the form of a lacquer which forms a hard film upon the surface to which it is applied and is not readily wiped off.

The antiseptic compositions of the present invention are generally capable of sanitising surfaces from a broad spectrum of pathogens. The composition is particularly effective against spore forming bacteria. An example of such a spore forming bacteria is *C. difficile*. However, the composition may also be effective against other pathogens such as MRSA, *P. aeurginosa*, *C. albicans* and *A. niger*.

Following is a description, by way of example only, with reference to the accompanying figures, of a method of putting the invention in to effect, wherein:

FIG. 1 schematically shows a germinate/exterminate protocol used in the prior art.

FIG. 2 shows the log reduction in CFU/mL of *C. difficile* NCTC 11204 spores exposed to different germinant solutions for one hour, followed by heat shocking for 10 minutes.

FIG. 3 shows log reduction in CFU/mL of *C. difficile* NCTC 11204 spores after one hour's exposure to each amino acid germinant solution, followed by heat shocking for 10 minutes at 70° C.

FIG. 4 shows the effect of an amino acid combination (arginine, aspartic acid, glycine and histidine) concentration in a germinant solution also containing 6.9 mM sodium taurocholate after 1 hour incubation with *C. difficile* spores of ribotype 027, 001, 106 and strain NCTC 11204.

FIG. 5 shows the log reduction in CFU/mL of spores of different strains of *C. difficile* after one hour exposure to different germinant solutions, followed by 10 minutes heat shock.

FIG. 6 shows the effect of pH on the germination of *C. difficile* NCTC 11204 spores in Tris buffer containing 10 mM arginine, aspartic acid, histidine and glycine and 6.9 mM sodium taurocholate.

FIG. 7 shows the log reductions in CFU/mL of *C. difficile* spores after 1 hr exposure to different germinant solutions, followed by either heat shock or chilling on ice (AA=amino acids, ST=sodium taurocholate, BZC=benzalkonium chloride, BZA=benzyl alcohol).

FIG. 8 shows the log reductions in CFU/mL of *C. difficile* spores after 1 hr exposure to different germinant solutions, followed by either heat shock or chilling on ice (CHG=chlorhexidine digluconate).

FIG. 9 shows the count of *C. difficile* vegetative cells in PBS (control) culture. 100% of the count is spores after 24 hrs FIG. 10 shows the count of *C. difficile* vegetative cells in a germination solution of the invention. After 72 hrs 100% of the count is still vegetative cells.

FIG. 11 shows the log reductions in CFU/mL of *C. difficile* spores after 1 hr exposure to different germinant solutions, followed by either heat shock or chilling on ice.

EXAMPLE 1—COMBINATIONS OF AMINO ACIDS FOR GERMINANT SOLUTION

Strains of *C. difficile*

A ribotype 106 strain (18587), a ribotype 001 strain (8565) (Health Protection Agency, North East UK) and the NCTC 11204 reference strain were used together with three ribotype 027 strains; R20291 (Anaerobic Reference Laboratory, Cardiff), 18040 and 15900 (HPA, North East UK).

Preparation of *C. difficile* Spore Suspensions

Spores of *C. difficile* were prepared as previously described (Shetty et al., 1999). A blood agar plate was inoculated with the relevant strain of *C. difficile* and incubated anaerobically (MiniMACS anaerobic work station, Don Whitley, Shipley, UK), for 72 hours, at 37° C. The plate was then removed and left in air, at room temperature for 24 hours, before harvesting all colonies and placing in 10 mL of 50% saline (0.9% w/v) and 50% methylated spirits. The suspension was vortex mixed thoroughly before being filtered through glass wool and was stored at 4° C. until use. Before each experiment spore suspension were centrifuged at 13000 rpm for 5 minutes and resuspended in sterilised distilled water (SDW).

Amino Acids

The following amino acids were used in the experiments detailed below: glycine, L-isoleucine, L-proline, D-alanine, L-glutamic acid, L-erine, L-threonine, L-spartic acid, L-arginine, L-valine, L-leucine, L-glutamine, L-tryptophan and L-asparagine (all from Sigma-Aldrich, UK), L-lysine, L-histidine and L-methionine (BDH), L-β-phenylalanine (Fisons) and L-cysteine (Fluka). Tyrosine was not tested as it did not dissolve in distilled water.

Efficacy of Different Amino Acids as Co-Germinants Against the Spore of C. difficile All germinant solutions contained 0.4% (w/v) of the amino acid (concentration of glycine used in previous study (Wheeldon et al., 2008)) and with 13.8 mM (w/v) sodium taurocholate (Sigma-Aldrich, UK), (double the physiological concentration in the duodenum (Leverrier et al., 2003)), which were dissolved in distilled water and sterilised by autoclaving at 121° C. for 15 minutes. Double strength thioglycollate medium (Oxid, UK), containing 13.8 mM sodium taurocholate (ST) was also tested for comparison against the other germinant solutions. One hundred microliters of each germinant solution was then added to 100 μL if C. difficile spores (containing $10^6$ CFU/mL) and was vortex mixed thoroughly. After one hour the entire 200 μL volume was added to 9.8 mL of Wilkins Chalgren broth (Oxoid, UK), equilibrated to either 70° C. for 10 minutes or chilled on ice. After appropriate dilution, 1 mL samples were placed in sterile Petri dishes before the addition of 15 mL of molton Fastidious Anaerobe Agar (FAA) (Lab M, UK), containing 0.1% (w/v) ST and 5% (v/v) defibrinated horse blood. The plates were mixed thoroughly before being incubated anaerobically for 48 hours, at 37° C. This method was adapted from Levinson and Hyatt (1966).

Determination of the Optimum Concentration of Amino Acids Required for the Germination of C. difficile Spores Arginine, aspartic acid, glycine and histidine were prepared at 200, 20, 2, 0.2 and 0.02 mM, together with 13.8 mM ST (which is double the strength required as they are diluted 1:2 during the experiment) and were dissolved in distilled water. All solutions were heated until dissolved and were sterilised by autoclaving. The same method as above was used to test the different concentrations of germinant solutions against the spores of C. difficile NCTC 11204, ribotype 027 (R20291), 001 and 106.

Efficacy of Amino Acids and Taurocholate Against the Spore of Six Different Strain of C. difficile Arginine, aspartic acid, glycine and histidine (at 20 mM w/v) were added separately or in combination to 13.8 mM (w/v) ST and dissolved by heating in distilled water, before sterilisation by autoclaving. The same method as described above was used to determine the efficacy of these amino acid solutions against the spores of C. difficile ribotype 001, 106, 027 (R20291, 15900 and 18040) and NCTC 11204.

Effect of pH of Buffered Germinant Solutions on the Germination of C. difficile Spore Arginine, aspartic acid, glycine and histidine (at 20 mM w/v), 13.8 mM (w/v) ST and 200 mM (w/v) Tris was dissolved in distilled water and adjusted to pH 5, 6, 7, 8 and 9 using hydrochloric acid before sterilisation by filtration (0.2 μm) or autoclaving. The same method as above was used to test each buffered solution against the spores of C. difficile NCTC 11204.

EXAMPLE 2—EFFECT OF GERMINANT SOLUTION WITH ANTIMICROBIAL AND PRESERVATIVE ON C. DIFFICILE

Germinant Solution

A solution containing 100 mM (w/v) glycine, histidine, valine, aspartic acid and arginine, 13.8 mM (w/v) sodium taurocholate, 100 mM (w/v) Tris buffer, 0.04% (w/v) benzalkonium chloride, 2% (v/v) benzyl alcohol was made up to the required volume with distilled water and adjusted to pH 7 using hydrochloric acid. The solution was heated and mixed thoroughly to dissolve all of the components before filtration through a pore size of 0.2 μm for sterilization. (This solution is double the working strength as it is diluted 1:2 during the experiment).

Preparation of C. difficile Spore Suspensions

Preparations of C. difficile Spores were Prepared as Noted Above.

Neutraliser

The neutraliser was adapted from Espigares et al., (2003) and contained the following: 120 mL (v/v) Tween 80, 25 mL (v/v) of 40% sodium metabisulphite, 15.69 g (w/v) sodium thiosulphate pentahydrate, 10 g (w/v) L-cysteine, 4 g (w/v) lecithin and made up to 1000 mL with distilled water. The pH was adjusted to 7 and was autoclaved to sterilize.

Germination Efficacy Testing

One hundred microliters of the germinant solution (as described above) was added to 100 μL of C. difficile spores (containing $10^6$ CFU/mL) and was vortex mixed thoroughly. For the control, 100 μL of sterilized distilled water was mixed with 100 μL of C. difficile spore suspension. Spore suspensions were also incubated with solutions containing benzalkonium chloride and Tris buffer (without amino acids or taurocholate), benzyl alcohol with Tris buffer (without amino acids and taurocholate) and a solution containing the five amino acids and taurocholate (with no antimicrobials). After one hour the entire 200 μL volume was added to 9.8 mL of neutraliser (as described above), equilibrated to either 70° C. for 10 minutes (heat shock to kill germinating cells) or chilled on ice (controls). After appropriate dilutions, 1 mL samples were placed in sterile petri dishes before the addition of 15 mL of molten Fastidious Anaerobe Agar (FAA) (Lab M, UK), containing 0.1% (w/v) ST and 5% (v/v) defibrinated horse blood. The plates were mixed thoroughly before being incubated anaerobically for 48 hours, at 37° C. (miniMACS Anaerobic Workstation (Don Whitley Scientific Ltd)). This method was adapted from a previous study by Levinson and Hyatt (1966).

Results and Discussion

Efficacy of Other Amino Acids as Co-Germinant with Glycine Against the Spores of C. difficile NCTC 11204

Incubation of C. difficile NCTC 11204 spores with arginine, aspartic acid or histidine with glycine and ST produced large log reductions in CFU/mL of 2.78 (99.8%), 3.06 (9.99%) and 3.12 (99.9%) respectively after heat shocking. Valine (with glycine and ST) and leucine (with glycine and ST) produced log reductions in CFU/mL of 1.72 (98.1%) and 1.62 (97.6%) respectively, which were similar to that of glycine and ST alone (1.85 log reduction (98.6%)). All other amino acids tested produced log reductions smaller than that of glycine and sodium taurocholate alone.

Efficacy of Co-Germinants Alone and in Combination with Glycine and Sodium Taurocholate Against the Spore of C. difficile NCTC 11204

When the four most effective amino acids from the initial screening (arginine, aspartic acid, histidine and glycine) were placed together in solution with ST and incubated with C. difficile spores, a greater log reduction in CFU/mL of 3.71 (99.9%) was produced after heat shocking, compared with when spores were incubated with either arginine, aspartic acid or histidine with ST, but without glycine there was less than one log reduction produced by each solution.

Determination of the Optimum Concentration of Amino Acids Required for the Germinations of C. difficile Spores Clostridium difficile spore germination was optimum in all strains tested when the amino acid concentration was between 10 and 100 mM. Below this concentration, germination of *C. difficile* spores was significantly reduced with less than a one log reduction observed at 0.1 mM and below. In all strains of *C. difficile* there was a significant reduction in CFU/mL observed when spores were exposed to 100 mM of amino acids without heat shocking.

Efficacy of Amino Acids and Sodium Taurocholate Against the Spores of Different Strains of *C. difficile* PCR Ribotype 027

All strains of *C. difficile* PCR ribotype 027 exposed to the four amino acids in combination with ST produced log reductions similar to those produced when spores were exposed to thioglycollate medium and ST. Both aspartic acid and histidine increased the log reduction in CFU/mL observed in each ribotype 027 strain when combined with glycine and sodium taurocholate, however, arginine did not cause any further increase in log reduction in CFU/mL when added to glycine and ST. Most interestingly, the two clinical strains (18040 and 15900) gave significantly larger log reductions in response to the thioglycollate medium or the four amino acids combined with ST compared with the R20291 strain.

Efficacy of Amino Acids and Sodium Taurocholate Against the Spores of Six Different Strain of *C. difficile*

The greatest log reductions in CFU/mL were observed with the NCTC 11204 reference strain of *C. difficile* after exposure to the amino acid and thioglycollate solutions. PCR ribotype 001 gave very similar log reduction values to the R20291 strain of PCR ribotype 207 in each of the different combination of germinant solution tested. For example, log reductions in CFU.mL of 2.12 (99.2%) and 1.98 (99%) were produced in *C. difficile* ribotype 001 and 027 R20291 respectively, after incubation with the four amino acids and ST, followed by heat shock.

Effect of pH of Buffered Germinant Solutions on the Germination of *C. difficile* NCTC 11204 Spores The pH of the buffered germinant solution greatly affected the log reduction in CFU/mL produced after incubation with the amino solution (and ST), followed by heat shock. At an acidic pH of 5, the germination solution did not produce any log reductions in CFU/mL, where as a 3.32 log reduction in CFU/mL (99.9%) was observed at a neutral pH of 6.98; which was found to be the optimum pH. A more alkaline pH of 8.81 did decrease the log reduction in CFU/mL observed, but to a much smaller extent than that of an acidic pH.

Effect of Germinant Solution with Antimicrobial and Preservative on *C. difficile*.

Over a 3 log reduction in CFU/mL (99.9% reduction) was produced after *C. difficile* spores were incubated with a mixture of amino acids and taurocholate in Tris buffer for 1 hour followed by heat shocking. However, without heat shocking there was very little reduction (0.13 log reduction) in the number of remaining spores after incubation with the amino acid solution. Incubation of *C. difficile* spores with a solution containing benzalkonium chloride in Tris or benzyl alcohol in Tris induced a very low log reduction in CFU/mL of less than 0.3 both with and without heat shocking. However, when *C. difficile* spores were incubated with a solution containing amino acids, taurocholate, benzalkonium chloride and benzyl alcohol in Tris, there was a 2.77 log reduction in CFU/mL (99.8% reduction) with ice treated spores and a 2.99 log reduction in CFU/mL (99.9% reduction) with heat shocked spores.

The inventors have also shown that EDTA and choloro-hexidine inhibit the germinant solution, where as benzalkonium chloride and benzyl alcohol do not affect germination. Benzalkonium choloride and benzyl alcohol were not sporicidal and did not initiate germination. Non heat-treated spores were killed after 1 hr incubation with benzalkonium choloride, benzyl alcohol, amino acid and sodium taurocholate and spores appear to be killed as they germinate with the germinant solution containing benzalkonium chloride and benzyl alcohol.

The neutraliser was found to be non-toxic towards *C. difficile* cells and other bacteria and was effective at nullifying the activity of the antimicrobials. Therefore the reduction in CFU/mL produced after 1 hr incubation with benzalkonium chloride, benzyl alcohol, amino acid and sodium taurocholate is not likely to be the result of a 'carry over' effect on the agar plates.

The present inventors have also found that benzalkonium chloride and benzyl alcohol do not affect the efficacy of the germinant solution. Benzalkonium chloride and benzyl alcohol therefore show preservative efficacy and appear to kill germinating spores of *C. difficile*.

Inhibitory Effect of Germination Solution on Spore Formation

The results shown in FIGS. 9 and 10, indicate that after 72 hrs of culture in the presence of the germination solution 100% of the count is still vegetative cells whilst in the control (cultured cells in PBS), 100% of the count are spores after 24 hrs. These results demonstrate that the germination solution of the invention prevents sporulation in vegetative cells of *C. difficile*.

The invention claimed is:

1. A method of sterilising or disinfecting an abiotic surface such that it is essentially free of pathogens, the method comprising: contacting the abiotic surface with an antiseptic composition comprising a germinant and an antimicrobial agent, wherein the germinant comprises sodium taurocholate and at least two amino acids selected from the group consisting of histidine, arginine, aspartic acid, glycine and valine, and wherein the antimicrobial agent comprises benzalkonium chloride and benzyl alcohol;

wherein the abiotic surface is contacted for a sufficient time for the pathogens to germinate and be killed;

wherein the antimicrobial agent is provided in an amount of from 0.01% to 2%;

wherein the amino acids are in an amount of from about 10 to about 100 mM based on the final composition;

wherein the antiseptic composition prevents sporulation of vegetative cells.

2. The method of claim 1, wherein the antiseptic composition is impregnated into a wipe comprising a fabric, mesh or gauze type material.

3. The method of claim 1, wherein the antiseptic composition is in the form of a hand wash, paint or lacquer.

4. The method of claim 1 wherein the composition is effective against bacterial pathogens selected from the group consisting of *C. difficile*, methicillin resistant *Staphylococcus aureus* (MRSA), *E. coli, Pseudomonas aeruginosa, Candida albicans* and *Aspergillus niger.*

5. The method of claim 1 wherein the germinant comprises histidine, arginine, aspartic acid, glycine and valine.

6. The method of claim 1 wherein the antiseptic composition is in a buffered solution.

7. The method of claim 1 wherein the antimicrobial agent consists of benzalkonium chloride and benzyl alcohol.

8. The method of claim 1 wherein the pH of the antiseptic composition is from about 6.04 to about 8.81.

9. The method of claim 1 wherein the amino acids include glycine and at least one further amino acid selected from the group consisting of histidine, arginine, aspartic acid and valine.

10. The method of claim 1 wherein the amino acids are in an amount effective to stimulate germination of spores.

\* \* \* \* \*